(12) United States Patent
Hodges (10) Patent No.: US 8,591,814 B2
(45) Date of Patent: Nov. 26, 2013

(54) SAMPLE PLATE FOR FLUID ANALYSIS IN A REFINERY PROCESS

(75) Inventor: Michael Graham Hodges, Wonersh (GB)

(73) Assignee: BP Oil International Limited, Middlesex (GB)

( * ) Notice: Subject to any disclaimer, the term of this patent is extended or adjusted under 35 U.S.C. 154(b) by 638 days.

(21) Appl. No.: 12/223,340

(22) PCT Filed: Jan. 17, 2007

(86) PCT No.: PCT/GB2007/000127
§ 371 (c)(1),
(2), (4) Date: Jul. 29, 2008

(87) PCT Pub. No.: WO2007/085797
PCT Pub. Date: Aug. 2, 2007

(65) Prior Publication Data
US 2009/0011517 A1 Jan. 8, 2009

(30) Foreign Application Priority Data
Jan. 30, 2006 (EP) .................................. 06250495

(51) Int. Cl.
*G01N 33/22* (2006.01)
(52) U.S. Cl.
USPC .......... 422/68.1; 436/139; 422/82.05; 422/89
(58) Field of Classification Search
USPC ..................... 422/68.1, 82.05, 89; 436/139
See application file for complete search history.

(56) References Cited

U.S. PATENT DOCUMENTS

| 3,996,786 | A | * | 12/1976 | Mead et al. ................ 374/27 |
| 5,449,603 | A | * | 9/1995 | Nielson et al. ............. 435/6 |
| 6,137,501 | A | * | 10/2000 | Wen et al. ............. 346/140.1 |
| 6,270,641 | B1 | | 8/2001 | Griffiths et al. |
| 7,270,784 | B2 | * | 9/2007 | Vuong et al. ............. 422/63 |
| 2002/0058273 | A1 | * | 5/2002 | Shipwash .................. 435/6 |

(Continued)

FOREIGN PATENT DOCUMENTS

| EP | 1 258 720 | 11/2002 |
| JP | 2003-194827 | 7/2003 |
| JP | 2005-130851 | 5/2005 |
| WO | 2005/068970 | 7/2005 |

OTHER PUBLICATIONS

International Search Report for PCT/GB2007/000127 mailed Jun. 3, 2007.
Written Opinion for PCT/GB2007/000127 mailed Jun. 3, 2007.

(Continued)

*Primary Examiner* — Paul Hyun
(74) *Attorney, Agent, or Firm* — Nixon & Vanderhye (57) ABSTRACT

Equipment for analyzing a fluid selected from a hydrocarbon fluid, a refinery feedstock, a refinery intermediate, a product of a refinery process, or a component or reaction product thereof, having a portable apparatus containing at least two different analytical devices, each device being able to analyze the fluid. A sample plate is provided in association with the portable apparatus which has a receiver for a fluid to be analyzed, at least two fluidic channels, at least one sensor capable of responding to a physical or chemical property of the fluid, and/or at least one sample cell, and at least one additional fluidic channel for transferring a portion of the fluid or a component or reaction product thereof from the receiver to the at least one sensor and/or sample cell.

22 Claims, 5 Drawing Sheets

(56) References Cited

U.S. PATENT DOCUMENTS

| | | |
|---|---|---|
| 2002/0076806 A1 | 6/2002 | Van Gelder |
| 2003/0027225 A1 | 2/2003 | Wada et al. |
| 2003/0072682 A1* | 4/2003 | Kikinis ........................ 422/100 |
| 2004/0098202 A1* | 5/2004 | McNeil et al. ................. 702/12 |
| 2004/0126279 A1* | 7/2004 | Renzi et al. ................... 422/100 |
| 2004/0224422 A1* | 11/2004 | Bonne et al. .................. 436/177 |
| 2005/0106742 A1 | 5/2005 | Wahl |
| 2005/0255001 A1 | 11/2005 | Padmanabhan et al. |

OTHER PUBLICATIONS

International Preliminary Report on Patentability mailed May 29, 2008.

\* cited by examiner

SAMPLE PLATE FOR FLUID ANALYSIS IN A REFINERY PROCESS

This application is the U.S. national phase of International Application No. PCT/GB2007/000127 filed 17 Jan. 2007 which designated the U.S. and claims priority to European Patent Application No. 06250495.6 filed 30 Jan. 2006, the entire contents of each of which are hereby incorporated by reference.

This invention relates to a sample plate for use with a portable apparatus for analysis of a fluid, for example a refinery feedstock, a refinery intermediate, or a product of a refinery process.

BACKGROUND OF THE INVENTION

Feedstock analysis, for example crude oil assay, is an important analysis that is typically performed before feedstocks are purchased for or refined in an oil refinery. Typically, an oil refinery will refine a large number of different feedstocks, including different crude oils, and blends of crude oils, each of which may differ in a number of important properties. In order to ascertain the optimum conditions for refining of each feedstock and to evaluate the potential value of a feedstock, such as the product yields, qualities and values obtainable, and the potential effects on the refining process of said feedstock, such as corrosion or deposition, often a large number of properties need to be analysed.

Traditionally, this has been a time-consuming analysis, requiring a relatively large volume of material and taking 1-2 weeks to produce a full set of analysis (assay) data. It is not uncommon for feedstocks to be purchased without a full assay being available to the purchaser, and, hence, the purchaser must make a number of assumptions on the value of the feedstock, for example, for a crude oil this may be based on knowledge of previous crude oils from similar regions.

It would be advantageous if a refinery feedstock analysis, preferably a full assay, were rapidly available to the potential purchaser or refinery operator.

In addition, rapid analysis of products of refinery processes is also desirable. Such products include intermediates in the overall refinery process, bitumen, products from the overall refinery process which are subsequently used as chemical feedstocks and products from the overall refinery process which are subsequently used as fuels or lubricants, or as blending components for fuels or lubricants, as well as the fuels (e.g. aviation, gasoline, diesel and marine fuels) and lubricants themselves. In addition, rapid analysis of formulated products, fuels and lubricants is desirable, for example at a terminal, at a pipeline, in the distribution system, or at a point of sale. Descriptions of refinery processes, and the products therefrom, are well-known to the person skilled in the art, and are described, for example, under the chapter entitled "Oil Refining", by Walther W. Irion and Otto S. Neuwirth, in Ullmann's Encyclopedia of Industrial Chemistry, published by Wiley.

Our earlier copending application no. PCT/US2005/033240 describes a portable apparatus for analysis of a refinery feedstock or a product of a refinery process, said apparatus comprising:
(a) a first analytical device for determination of the boiling point profile of a refinery feedstock or a product of a refinery process, and
(b) at least two further analytical devices each of which contains or is associated with a database and an algorithm, at least one of said devices being adapted for determination of the density of the refinery feedstock or product of a refinery process, and at least one of said devices being adapted for determination of the total acid number (TAN) of the refinery feedstock or product of a refinery process.

Further, our earlier copending application no. PCT/US2005/033247 discloses a method of assaying a hydrocarbon-containing feedstock, the method comprising:
(a) measuring boiling profile and at least one other property of the hydrocarbon containing feedstock with at least two different laboratory-independent techniques wherein each laboratory-independent technique is selected to be predictive of each respective property;
(b) transmitting the measurements made in step (a) to a processor capable of reconstructing a determinative assay of the hydrocarbon-containing feedstock from the measurements; and,
(c) reconstructing a determinative assay of the crude oil from the measurements. This method can advantageously be carried out using the apparatus of PCT/US2005/033240.

SUMMARY OF THE INVENTION

We have now found an improved method for providing samples to apparatus such as that claimed in PCT/US2005/033240.

Accordingly, the present invention provides a sample plate for use with a portable apparatus containing at least two different analytical devices, said plate comprising (i) a receiver for a fluid to be analysed; (ii) at least two fluidic channels each adapted to transfer a portion of said fluid or a component or reaction product thereof from said receiver to one of said analytical devices contained in said associated portable analysis apparatus; (iii) at least one sensor capable of responding to a physical or chemical property of said fluid or a component or reaction product thereof, and/or at least one sample cell suitable for containing a sample of said fluid or a component or reaction product thereof for spectroscopic or optical analysis; and (iv) at least one additional fluidic channel adapted to transfer a portion of said fluid or a component or reaction product thereof from said receiver to said at least one sensor and/or sample cell.

The sample plate according to the invention provides the dual function of sample preparation for an analytical apparatus, and also provides some analytical capability itself by virtue of the sensor(s) and/or sample cell(s) it contains. In combination with the portable apparatus, the sample plate of the invention forms an equipment set for analysing a fluid, which comprises a sample plate of the invention, in association with a portable apparatus containing at least two different analytical devices. Suitably, means are provided for attachment of said sample plate to said apparatus. Said attachment means may for example be of the click-fit type or slot in type, or they may involve the use of a hinged flap (which may contain additional control, sensing or analytical devices). Mechanism for permitting relative sliding or rotating movement, for example a rotating wheel or turntable, to bring different parts of the plate into line with different components of the portable analytical apparatus, may be provided.

The sample plate and equipment set of the invention are very easy to use. In use, a user merely selects a suitable sample plate, and attaches it to the associated portable analysis apparatus. Appropriate fluidic channels of the sample plate are adapted to link up with the associated analysis devices in the portable apparatus, and the sensor(s) and/or sample cell(s) in the sample plate is/are adapted to link up with any associated electronic circuitry and/or spectroscopic or optical analysis means, which may also be present in the portable apparatus. In use, the user merely has to add the fluid to be tested to the receiver of the sample plate, and analysis of the sample can then be performed.

The sample plate can be reused, suitably after being cleaned. Alternatively, because the sample plate of the invention can in some embodiments be constructed very cheaply, it may be regarded as disposable. Thus, a plurality of sample plates may be provided in association with a single portable apparatus. Each sample plate may be intended for single use, being disposed of after said use, or for a small number of uses. Use of a fresh plate on each occasion of use prevents problems arising from contamination of the plate with previous samples of fluid. All of the plurality of sample plates may have the same construction. Alternatively, the plurality of sample plates may include two or more different types of plate having different construction, the construction of each type of plate being adapted for use with a particular type of fluid to be analysed. For example, in the field of oil refining, one type of sample plate may contain one or more sensors and/or sample cells and/or micro fluidic elements particularly suitable for use in analysing a particular product of a refinery, for example diesel fuel or gasoline, while a different type of sample plate may contain one or more sensors and/or sample cells and/or micro fluidic elements particularly suitable for use in analysing crude oil. Suitable connections for each sensor and/or sample cell to an appropriate piece of associated electronic circuitry and/or spectroscopic or optical analysis means can also be provided. For example, an analytical apparatus may contain several different pieces of electronic circuitry associated with different sensors, or types of sensor. In a sample plate designed for use with one particular fluid, connections for any sensor in the sample plate to the appropriate piece of electronic circuitry present in the analytical apparatus will be provided. A sample plate for use with a different fluid may contain connections to different pieces of electronic circuitry present in the analytical apparatus. Similarly, appropriate links for any sample cell will be provided.

Thus, in a preferred embodiment of the invention, an equipment set is provided which comprises a portable analysis apparatus as described above together with a plurality of sample plates according to the invention. Said equipment set will be suitable for multiple use and/or suitable for use with different fluids.

The exact design of a sample plate according to the invention will depend upon the intended application. The exact path, nature and number of fluidic channels may be varied. The sample plate may have one or more micro pumps for transferring fluids between various parts of the sample plate. Suitable micro-pumps include gear pumps, diaphragm pumps, syringe pumps and peristaltic pumps. Where pumping of fluids is required, a micro pump driver may be located in the analytical apparatus to be used in association with the sample plate, such that in use the fluids on the sample plate are pumped in an appropriate fashion. The sample plate can comprise one or more microvalves to control the path and/or the quantity or proportion of fluids that are transferred between various portions of the sample plate. Where it is desired to separate the sample fluid into components before analysis, or where it is desired to carry out a chemical or physical transformation on the sample fluid before analysis, suitable means may be provided.

For example, the plate may contain fluidic devices for separation of components of the fluid, for example (i) micro fluidic/micro fractionation device for fractionation of a sample according to its boiling point, (ii) micro fluidic separation device such that the volatile portion of a fluid can be separated and sent to a different micro analytical device or sensor (head space analysis), (iii) a micro chromatographic element (e.g. solid liquid chromatography, electrophoresis, ion-exchange, ligand exchange) such that specific types of fluid components may be separated for analysis by a micro analytical device or sensor, (iv) a micro fluidic filter such that particulate matter may be separated from the sample either for sample clean up prior to analysis by a sensor or micro analytical device or for separation of the solid for suitable analysis or to obtain a solid free liquid for analysis, and/or (v) a micro mixer and separator whereby liquids (reagents, solvents etc) may be mixed with the sample, for example to cause a reaction, complex formation, precipitation or sedimentation, or liquid/liquid separation. The onset or rate of precipitation may be monitored via a suitable spectroscopic (e.g. UV, NIR), or optical (e.g. light scatter) technique. A mixture of solids and liquids may be separated using a suitable micro separation device, the liquid being passed to a suitable sensor or micro analytical device. When a solid is formed by precipitation this may be filtered from the mixture using a micro filter or other micro separation device, or the solid may be redissolved and transferred to a suitable sensor or micro analytical device.

The liquids obtained from a first separation or clean up may be subjected to further separation or clean up prior to analysis by a sensor or micro analytical device. Liquids obtained from a first separation may be mixed with further liquids to effect, for example, reaction, complex formation, precipitation or sedimentation, or liquid/liquid extraction. For example, very polar material may be removed by passing over a solid phase adsorbent, and the cleaned-up liquid oxidised using a suitable reagent in a micro mixer.

Reaction, or complex formation, or liquid extraction products may be analysed by a suitable spectroscopic device, e.g. by UV absorption spectroscopy to determine the concentration of a specific component.

Reagents may be added to a sample in a controlled way in a mixer cell coupled directly to an electrochemical/conductivity sensor such that an electrochemical titration is effected. Such processes may be used for determination of Bromine Number, TAN or total base number.

Portions of additional liquids (reagents, solvents etc) can be stored on the sample plate or elsewhere in the equipment set. Storing the additional portions of liquid on the sample plate helps to minimise and contain solvents and other reagents used in analysing the sample. For example, different plates may contain different liquids required for specific analyses of specific samples, and thus different analyses can be performed successively using a single portable apparatus but different sample plates. In this way, only the specific liquid required for a particular analysis, in the amount needed for that analysis, needs to be stored.

In an alternative embodiment, additional liquids are instead introduced by other means, for example by being pumped or injected into one or more fluidic channels on the sample plate. In one embodiment, this can be achieved by attaching to the sample plate a cartridge containing pre-measured portions of any additional liquids required for the treatments and analyses to be carried out by the equipment set. Using an easily replaceable device such as a cartridge reduces the complexity of apparatus required, which facilitates.

Portions of the plate may be differentially heated or cooled (e.g. from contact with heaters or coolers in the portable analytical device), for example to aid fluid flow or to induce reaction or precipitation of components. In one embodiment, a zone may be provided where a solvent is mixed with a sample fluid such that on cooling wax is precipitated, which can if desired be monitored for example by optical methods (for example light scattering).

The sample plate according to the invention may contain one or more sample cells for spectroscopic or optical analysis of the fluid, or separated or reacted portions of the fluid. Such a sample cell will form part of a suitable micro analytical device. An electromagnetic radiation source (IR, NIR, Visible, UV) may be placed on one side of the plate (e.g. via a probe which locates into the top surface of the plate), and a suitable detector on the other (lower side) of the plate. Radiation passes through the sample cell, from the probe, and into the detector, the sample cell being made of suitable transmittance materials. The cell path length (distance of sample through which the radiation passes) is controlled by the design of the plate. Adsorption at a particular wavelength or over a range of wave lengths may be used to monitor specific compounds or a range of compounds in the sample fluid.

The sample plate according to the invention may be made of plastic, ceramic, glass, metal or other suitable micro fabrication materials, or mixtures thereof. The material is selected such that minimal or no degradative effects such as leaching, distortion, dissolution, reaction or etching takes place when in contact with the liquid sample, or other reagents such as solvents and precipitants. Plastics that are particularly suitable for hydrocarbon-based samples such as refinery feedstocks and products of refinery processes include Polyetheretherketone (PEEK) and Polymethylmethacrylate (PMMA). The fluid plate may be made by micro fabrication techniques, or using suitable micro fabrication compatible moulding techniques, or by a combination thereof.

The equipment set of the present invention may be used for analysis of any desired fluid, or a component or a reaction product of a fluid. Preferably it is used for the analysis of fluids associated with the petroleum or petrochemical industries, for example oil exploration, production, refining or marketing. Thus hydrocarbon fluids, exploration fluids, refinery feedstocks, refinery intermediates, products of refining such as fuels or lubricants, fluids used as treatments for or additives to such fluids. Preferably, it is used for analysis of a refinery feedstock, a refinery intermediate, or a product of a refinery process.

The refinery feedstock may be any suitable feedstock that may be fed to a refinery, such as a crude oil, a synthetic crude (syncrude), a biocomponent, an intermediate, such as a residue or a cracked stock, or blends of one or more of said feedstocks.

Preferably the refinery feedstock is a crude oil or blend of crude oils, optionally also comprising (blended with) one or more of a synthetic crude component, a biocomponent or an intermediate component, such as a residue component or a cracked stock component.

Where the sample plate of the present invention in association with a portable apparatus is used for analysis of a product of a refinery process, the product may be an intermediate stream in the overall refinery process, a bitumen, a product from the overall refinery process which is subsequently used as a chemical feedstock, a product from the overall refinery process which is subsequently used as a fuel or lubricant, or as a blending component for a fuel or lubricant, or a fuel, for example an aviation, gasoline, diesel or marine fuel or lubricant itself.

In one embodiment, the equipment set of the present invention permits the complete determinative assay of a refinery feedstock or a product of a refinery process from measurement only of the boiling point profile, density, and total acid number ("TAN") of the feedstock or product, optionally together with a measurement of sulphur content. Prior to the making of the inventions claimed in our copending application mentioned above, it was not appreciated that a complete assay could be obtained using only these parameters. Thus, in this embodiment of the equipment set of the present invention comprises one or more sample plates according to the invention in association with a portable apparatus for analysis of a refinery feedstock or a product of a refinery process, said apparatus comprising:

(a) a first analytical device for determination of the boiling point profile of a refinery feedstock or a product of a refinery process, and (b) at least one further analytical device associated with a database and an algorithm and capable of measuring at least one physical or chemical property of a refinery feedstock or a product of a refinery process; said equipment set being capable of determining at least the boiling point profile, the total acid number (TAN), and the density of a refinery feedstock or product of a refinery process.

The analytical devices present in the portable apparatus associated with a sample plate of the invention are suitably microfabricated, and may be in the form of sensors. Microfabricated devices are devices in which the crucial analytical part or detector of the device is fabricated using techniques consistent with the micro-chip industry, and such part produces a spectrum or a simple electrical signal, in response to contact with a test substance. This spectrum or simple electrical signal is fed to an associated set of electronics which converts the input signal into a value for the property being measured, using chemometric techniques, i.e. the input is fed to a relational database containing previous analytical measurements, and an algorithm correlates the input to provide the required property or properties. In general, sensors produce a simple electrical signal, are extremely small and cheap, and are used to measure a single property. A sensor will generally be provided with appropriate associated electronics. Other micro devices which produce a spectrum may be somewhat larger and more expensive, and may often be used to measure more than one property.

The sample plate according to the invention preferably contains at least one sensor. In a preferred embodiment of the invention, the set of electronics which would normally be associated with the sensor is located in the portable analytical device, and means are provided such that, in use, the sensor becomes connected with that set of electronics. In this way, the rather larger and more expensive set of electronics is retained for multiple use, while the very cheap sensor itself is located within the sample plate which may, as described above, be disposable. Similarly, if the sample plate contains a sample cell, the spectroscopic or optical analysis means associated with that sample cell, including any associated electronics, may be located in the portable analytical device.

The sample plate may contain more than one sensor and/or sample cell, and each such sensor and/or sample cell is preferably associated with a corresponding set of electronics and/or spectroscopic or optical analysis means located in the portable analytical device. Such sensors and/or sample cells are chosen to be appropriate to the fluid to be analysed, and the properties desired to be measured. A number of sensors or sample cells may be located together to form an array of sensors or sample cells. A sample of the fluid to be analysed is provided to each sensor and/or sample cell or to an array of sensors or sample cells by means of appropriate fluidic channels present in the sample plate. When the sample plate according to the invention is intended for use in the analysis of refinery feedstocks or products of a refinery process, sensors and/or sample cells may be included which enable the measurement of density, viscosity, chemical constitution such as acidity, etc.

In a portable analysis apparatus mentioned above, the first analytical device for determination of the boiling point profile may be capable of yielding the boiling point profile directly, but preferably yields the boiling point profile by using suitable software or models as described above, such as by reference to a suitable database comprising data of known samples, such as of known crude oils. By this means, very rapid analysis can be obtained in comparison with traditional methods, which require the oil to be physically separated into its components. The first analytical device preferably determines the true boiling profile (TBP) of a refinery feedstock or a product of a refinery process. The first analytical device is preferably selected from (i) a micro-distillation device, (ii) a micro-NIR spectrometer, (iii) a micro-oscillator device and (iv) a micro GC. The sample cell for use with any spectroscopic or optical device present in the portable apparatus may if desired be present on the sample plate designed for use with that apparatus. The apparatus also comprises at least one further analytical device, for example for measuring density and/or TAN. Preferably a device for measuring density is an oscillating sensor, and a device for measuring TAN is an electrochemical sensor. Each additional device may if desired also be capable of determining the boiling point profile, and preferably capable of determining the TBP, in addition to one or more further properties. For example, the first analytical device may be a micro-distillation device, and a second analytical device may be a micro-NIR spectrometer.

Thus, in a preferred embodiment, the equipment set of the present invention includes a portable apparatus comprising two or more, preferably three or more, analytical devices selected from a micro-distillation device, a micro-NIR spectrometer, a micro-oscillator device and a micro-GC. A portable apparatus containing at least one of a micro-distillation device, a micro-NIR spectrometer, a micro-oscillator device and a micro GC may also if desired contain an additional oscillating sensor and an electrochemical sensor; alternatively or in addition, an oscillating sensor and/or electrochemical sensor may be contained in a sample plate to be used in association with the analytical apparatus.

Typically, the equipment set comprising a sample plate in association with a portable apparatus, contains two, three or more devices selected from micro-distillation, micro-NIR, micro-oscillator and micro-GC devices, together with one or more sensors. Such an equipment set can provide a significant quantity of the analysis data required for a refinery feedstock assay or analysis of a product of a refinery process.

In addition, the equipment set may comprise a number of additional analytical devices to ascertain further required properties of the fluid to be analysed, for example a refinery feedstock or the product of a refinery process. Further, more than one device may be included in the set to measure a single property. This apparent redundancy may be very valuable as the results can be used to cross-check each other.

Further properties of a refinery feedstock or product of a refinery process which it may be desired to determine in addition to the boiling point profile, density and TAN will be sample dependent, and typically may include total base number (TBN), cold flow properties (such as pour point, freezing point and cloud point), viscosity, Research-Octane Number (RON), Motor Octane Number (MON), cetane number, smoke point, Bureau of Mines Correlation Index (BMCI), refractive index, conductivity, sulphur content (including thiophenic sulphur or specific thiophenic sulphur compounds), nitrogen content, nickel content, vanadium content and combinations thereof. Preferably the equipment set contains at least one additional device for determining one or more of these properties, and if this additional device comprises a sensor, it can be provided either as part of the sample plate or as part of the portable apparatus. For example, an additional device for determining sulphur content, for example a pyrolyser coupled with a micro GC and a micro mass spectrometer, and/or an additional device for determining metal content, may be provided.

Suitable devices for determination of said further properties may include micro conductivity/capacitance devices (e.g. for acidity), micro rheological devices (e.g. for viscosity) and micro spectroscopic devices, such as NIR, ion mobility/differential mobility, acousto-optical, acoustic, UV-Vis and Mid-IR spectroscopies (e.g. MID IR for naphthenic acidity). Micro-conductivity/capacitance devices, micro rheological devices, and acousto-optical devices are all available in the form of sensors and can be included, optionally as part of an array of sensors, in the sample plate of the invention, or in the portable apparatus. Sample cells for use with any spectroscopic device may be located either on the sample plate or in the portable apparatus. Where the sample is unchanged as a result of an analysis or treatment in a sample cell, a flow-through cell can be used, such that the analysed or treated sample can be subsequently transferred to another part of the sample plate for further analysis. A flow-through cell can also be used where a sample is changed, and the changed sample requires further treatment or analysis. Use of flow-through cells minimised the quantities of sample and other liquids such as solvents or reagents that are required for the analyses to be performed, and also minimises the quantity of sample fluids and additional liquids that require disposal after the analysis is complete.

Waste fluids, for example sample fluids treated with other reagents and after their analysis, can be transferred to and collected in a waste reservoir, which may be separate from the portable apparatus, or which may be directly associated with the portable apparatus or the sample plate.

The equipment set of the invention enables the determination of for example (i) specific volatile components, for example contaminants, in a feedstock or product, e.g. mercaptans, methanol, organo chloride, (ii) asphaltenes via precipitation, filtration, redissolution and UV measurement, (iii) asphaltene flocculation point via addition of non-solvent and spectroscopic or optical observation of the flocculation point, (iv) wax precipitation point via solvent addition cooling and observation of wax flocculation by optical means, (v) thiophenic sulphur via oxidation to sulphones, for example using a suitable reagent in a micro mixer, followed by separation or extraction of polar sulphones which may then be speciated; (vi) bromine number, TAN and total base number.

As mentioned above, a portable apparatus as described above, when used in association with a sample plate according to the invention, may be used to determine properties of a multi-component fluid, and/or properties of one or more constituents of the fluid, and/or properties of one or more reaction products of the fluid. For example, it may be used to measure boiling point profile, density and TAN, and optionally one or more additional properties, of a refinery feedstock or product of a refinery process as a whole, or it may be used to measure boiling point profile, density and TAN, and optionally one or more additional properties, of one or more fractions of the refinery feedstock or product of a refinery process.

Thus, in a further embodiment, the present invention provides an equipment set comprising a sample plate according to the invention in association with a portable apparatus for analysis of a multi-component fluid, said apparatus comprising:
(A) a micro-separation device for separation of the multi-component fluid into two or more components, and (B) two or more analytical devices for determination of two or more physical and/or chemical properties of one or more of the components.

A preferred example of this embodiment of the invention provides an equipment set comprising a sample plate according to the invention in association with a portable apparatus for analysis of a refinery feedstock or a product of a refinery process, said apparatus comprising:
(A) a micro-separation device, capable of determination of the boiling point profile of a refinery feedstock or a product of a refinery process, for separation of the refinery feedstock or product of a refinery process into two or more fractions, and
(B) two or more further analytical devices for determination of density and TAN of one or more of the fractions.

In this embodiment, the micro-separation device provides separation of the fluid into at least two components, and said components can then be analysed by two or more further analytical devices.

Preferably, the micro-separation device (A) is the first analytical device of the analytical apparatus of the present invention. Suitable micro-separation devices include a micro-distillation device and a microchromatographic device, such as a micro GC, micro LC (liquid chromatography) device or a micro size exclusion chromatography device.

Alternatively, the two or more further analytical devices of (B) may comprise said first analytical device, preferably for determination of the boiling point profile, preferably of the TBP, in addition to two or more analytical devices, preferably for the determination of density and TAN of the fractions. One or more further analytical devices may also be provided which can determine properties of the fluid before fractionation, for example the pre-fractionated refinery feedstock or product of a refinery process.

For example, the micro-separation device may be a micro-distillation device which is the first analytical device, and a second analytical device may be a micro-NIR spectrometer. The micro-NIR may be used, for example, to give data on density, amounts of saturates and aromatics in one or more of the fractions obtained from the micro-separation device, and, optionally, also in the total refinery feedstock or product of a refinery process.

Alternatively, or in addition, the further analytical devices may also comprise a number of other analytical devices, as described above, to ascertain further required properties of the total refinery feedstock or product of a refinery process and/or of the fractions.

Preferably the portable apparatus used in association with a sample plate according to the present invention is handheld, suitably having a total weight of less than 5 kg, such as 2 kg or less. The use of an equipment set according to the present invention requires only a small quantity of refinery feedstock or product of a refinery process (hereinafter the refinery feedstock or product of a refinery process may be referred to as "sample"), typically less than 100 ml, such as 10 ml or less, and preferably 1 ml or less. Because of the small quantity of sample required the analysis can be performed in a significantly shorter time than conventional analysis, such as conventional crude oil assay.

Typically, the equipment set according to the present invention provides an analysis in less than two hours, and preferably provides an analysis in less than 30 minutes, such as in less than 5 minutes.

Where present, a micro-distillation device may be any suitable device which can be utilised to distil the sample, for example to give fractions similar to those achieved by conventional distillation. For example, the micro-distillation device may distil a crude oil or other refinery feedstock to give fractions similar to those achieved by conventional refinery distillation in a crude distillation unit (CDU). The micro-distillation device may also be a micro engineered device comprising a micro-heater for vaporising the sample (e.g. crude oil), a suitable channel, for example a capillary, through which the vaporised sample passes, or a series of channels such that vapour liquid exchange is achieved (a counter current device), a suitable condensing zone (typically a cooled zone, such as a micro-refrigerator) on which vaporised sample that has passed up the channel condenses, and a micro-sensor to measure the condensation of sample at the condensing zone. The micro-sensor may be an optical sensor. Preferably, the micro-distillation device is a micro-fabricated separation device, for example, on a silicon wafer. The micro-distillation device may be disposable. Where the micro-distillation device provides a series of fractions similar to those achieved by conventional distillation, then these fractions can be analysed by one or more further analytical devices.

A micro-oscillator device, when present, is preferably an acoustic optical device or sensor. Micro-oscillator devices are based on measurement of the frequency of oscillation of the device, which changes with mass of material on the oscillator. Thus, if material evaporates or condenses on the device, the frequency changes. As well as information on boiling point profile, acoustic optical devices may provide information on viscosity, cold flow properties, volatile contaminants and deposits formation. Suitable micro-oscillators are described in U.S. Pat. No. 5,661,233 and U.S. Pat. No. 5,827,952.

Micro-NIR, when present, may be used, for example, to provide information on boiling point profile and to give a simulated distillation curve, as well as to provide information on density and amounts of saturates and aromatics, or water, in the sample as a whole and/or in fractions obtained from a suitable separation step, such as a micro-distillation device. Sulphur and/or cold flow properties, such as cloud point and freezing point, acidity (TAN), Research Octane Number (RON), Motor Octane Number (MON), cetane number and smoke point may also be measured. Suitable micro-NIR analysers include the Axsun NIR-APS Analyser produced by Axsun Technologies Inc., Massachusetts.

Micro-GC, when present, may provide a simulated distillation curve and can provide hydrocarbon speciation, such as of $C_1$-$C_9$ hydrocarbons. Suitable micro-GC devices include Siemens MicroSAM process GC's or SLS Micro-technology GC's.

Micro-ion mobility/differential mobility spectrometry, when present, may be used to provide information on polar molecules in the sample, for example contaminants such as organic chlorides or methanol, as well as sulphides and nitrogen compounds. Further, micro-ion mobility/differential mobility spectrometry coupled with a micro pyrolyser, can give enhanced nitrogen and sulphur analysis. Micro-ion mobility/differential mobility spectrometry is best implemented in combination with micro GC. Suitable micro-ion mobility/differential mobility spectrometers include the Sionex microDMx.

The present invention has the advantage that, due to their relatively small individual sizes and sample requirements, a number of different analytical devices may be arranged in a single equipment set. A sample plate together with an associated portable apparatus preferably includes at least 3 different analytical devices, at least one of which may be in the form of a sensor located on the sample plate, or which may include a sample cell located on the sample plate. Preferably at least 5 different analytical devices, such as at least 10 different analytical devices, are included, allowing a number of properties of a sample (or of fractions or reaction products thereof) to be ascertained, and providing a significant amount of data for analysis, either directly or via a suitable database model as described further below.

Thus, an equipment set according to the present invention can be taken to the location of the sample to be analysed, and a rapid analysis of the sample obtained. For example, for crude oil analysis (assay), the apparatus may be used for "at location" rapid assessment/valuation of crude oils, for example on a crude oil tanker or in a land-based crude oil storage tank, or at an oil exploration drilling or production site, allowing the value of the crude oil to a potential purchaser to be quickly ascertained. At an oil exploration drilling site, it may be used at the "well-head" on the drilling site to provide rapid analysis of a crude oil, for example, to provide rapid feedback of the properties of a crude oil at a test well allowing evaluation of said crude oil.

Because of the relatively small size of the components of the equipment set of the present invention, the power requirements are also relatively low. Hence, the equipment set may be operated from a suitable battery (or battery pack), preferably a rechargeable battery, without the battery requirements being too heavy to impact the portability of the apparatus.

Preferably the equipment set comprises, or is at least compatible with, wireless communications, such as a wireless mesh network, and more preferably, with remote communications means, such as satellite-based data communication, such that the analysis results may be readily communicated to the potential purchaser, again reducing the time-scale on which the analysis data is available to the potential purchaser.

Especially where suitable micro-devices are not available, the equipment set according to the present invention may be used in combination with other portable analysers, particularly those yielding elemental data, such as portable X-Ray Fluorescence (XRF) spectroscopy and Laser Induced Breakdown Spectroscopy (LIBS) to improve the breadth of assay.

XRF, for example, can provide analysis of sulphur and metals content of a sample, for example of crude oil fractions. Suitable, portable, XRF analysers include those available from OXFORD instruments Generally, a sample plate according to the present invention in association with a portable apparatus, optionally in combination with any other analysers, will generate data in respect of at least 10 key properties of the sample to be analysed, such as at least 20 key properties. For crude oil assay, for example, there is preferably provided data in respect of, or from which can be derived (as described further below), the majority of the key properties measured in a conventional crude oil assay, which include the boiling point profile, density, total acid number (TAN), cold flow properties (such as pour point and cloud point), viscosity, sulphur content, nitrogen content, nickel content, vanadium content and combinations thereof of the full crude oil and/or of fractions thereof. Similar properties are required for assay of other refinery feedstocks.

The analysis data obtained may directly generate sufficient analysis data, for example assay data for the crude oil being analysed.

Alternatively, the analysis data obtained may be enhanced via input to a suitable database model, typically a model derived from analysis data obtained from analysis of a large number of other samples. For example, for analysis of a crude oil, the analysis data obtained may be enhanced via input to a crude oil assay database model derived from assay data obtained from analysis of a large number of other crude oils. The crude oil assay database model may be used to generate a detailed assay with improved confidence.

Similarly, for analysis of a product from a refinery process, the data may be enhanced via input to a suitable database model of the product properties derived from analysis of a large number of similar (equivalent) products.

As an example, where the analysis data obtained is data from a multivariate analytical technique, such as NIR, the analysis data may be analysed by fitting the information to a linear combination of known multivariate analytical data in said database, such as described in WO 03/48759.

Because of the rapid analysis obtainable from the equipment set of the present invention, analyses can be obtained more often and/or can be used for process optimisation. For example, the equipment set may be used at a refinery and regular analyses can be performed on blends of refinery feedstocks, such as blends of crude oils, produced (from two or more sources available) at the refinery, to ensure optimum configuration of the refinery for the blend. Further the equipment set may be used to verify consistency and/or quality of feedstocks on arrival at a refinery or blending station and/or may be used to provide on-line or at-line determination of feedstock quality and property data for input to blending and process refinery optimisation models.

Where the equipment set of the present invention is used at the "well-head" on a drilling site, a number of sets may be operated at different well-heads which use a common transport mechanism, for example a common pipeline, to provide analysis of the crude oil from each well. Analysis of the individual crude oils and appropriate scheduling may allow more optimum composition of the final crude oil blend. In addition, by repeated analysis of the crude oils from different well-heads, changes in the individual crude oils with time can be used to predict the effects on the produced crude oil blend, or influence the blending to maintain a constant quality crude oil blend.

Similarly, where the equipment set is used for analysis of a product obtainable from a refinery process, the apparatus may be used to check consistency and quality of the product at the refinery, or at subsequent locations, such as at chemical plants themselves, at fuels blending terminals or in fuel-containing tanks, such as in fuel tankers or stationary tanks at airports, dockyards or on petrol station forecourts.

In a further aspect, the present invention also provides a method for analysis of a fluid, preferably a refinery feedstock, a refinery intermediate, or a product of a refinery process, said method comprising analysing the fluid using a sample plate according to the invention in association with a portable apparatus as previously described.

The method may also comprise analysis of the fluid with one or more further portable analysers, communication of the analysis results to a potential purchaser, and/or combination of the analysis information obtained with a database model as previously described.

BRIEF DESCRIPTION OF THE DRAWINGS

The invention is further illustrated by the accompanying schematic drawings, in which.

DETAILED DESCRIPTION OF PREFERRED EMBODIMENTS

Figure 1:
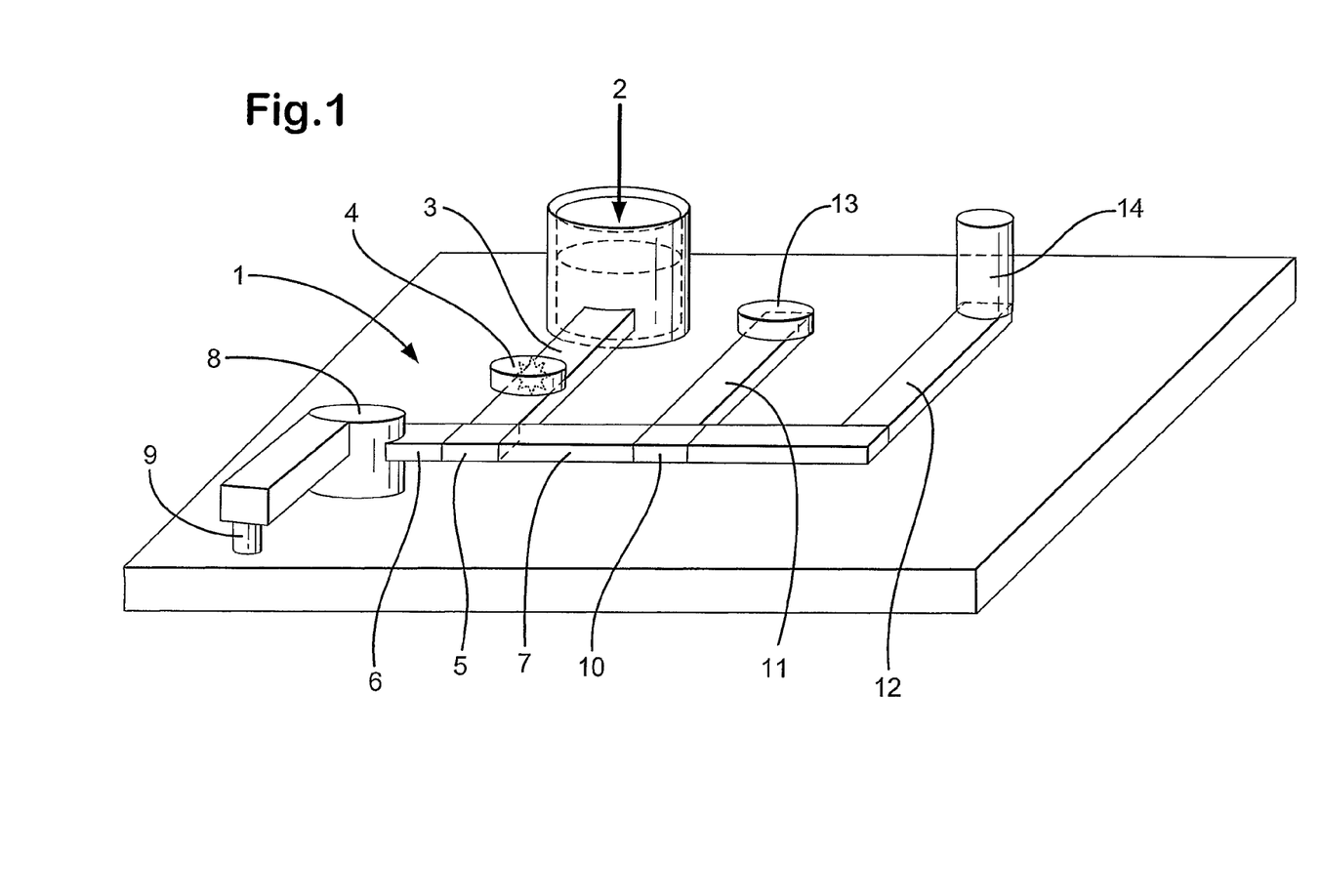
FIG. 1 illustrates a sample plate according to the invention.

Referring now to FIG. 1, a sample plate illustrated generally as 1 comprises a receiver 2 for a fluid to be analysed, in this case crude oil. A first fluidic channel 3 transfers crude oil from receiver 2 to a gear pump 4, by which the oil may be metered. The crude oil stream is then sent to a first micro valve 5 which controls the flow permitting the creation of first and second streams 6 and 7. First stream 6 passes to a head space generation device 8 and thence to an inlet 9 for a micro gas chromatography device. Second stream 7 passes to a second micro valve 10 which controls the flow permitting the creation of third and fourth streams 11 and 12. Third stream 11 is passed to an acidity sensor 13, while fourth stream 12 is passed to a sample cell 14 for a micro NIR spectrometer.

Figure 2:
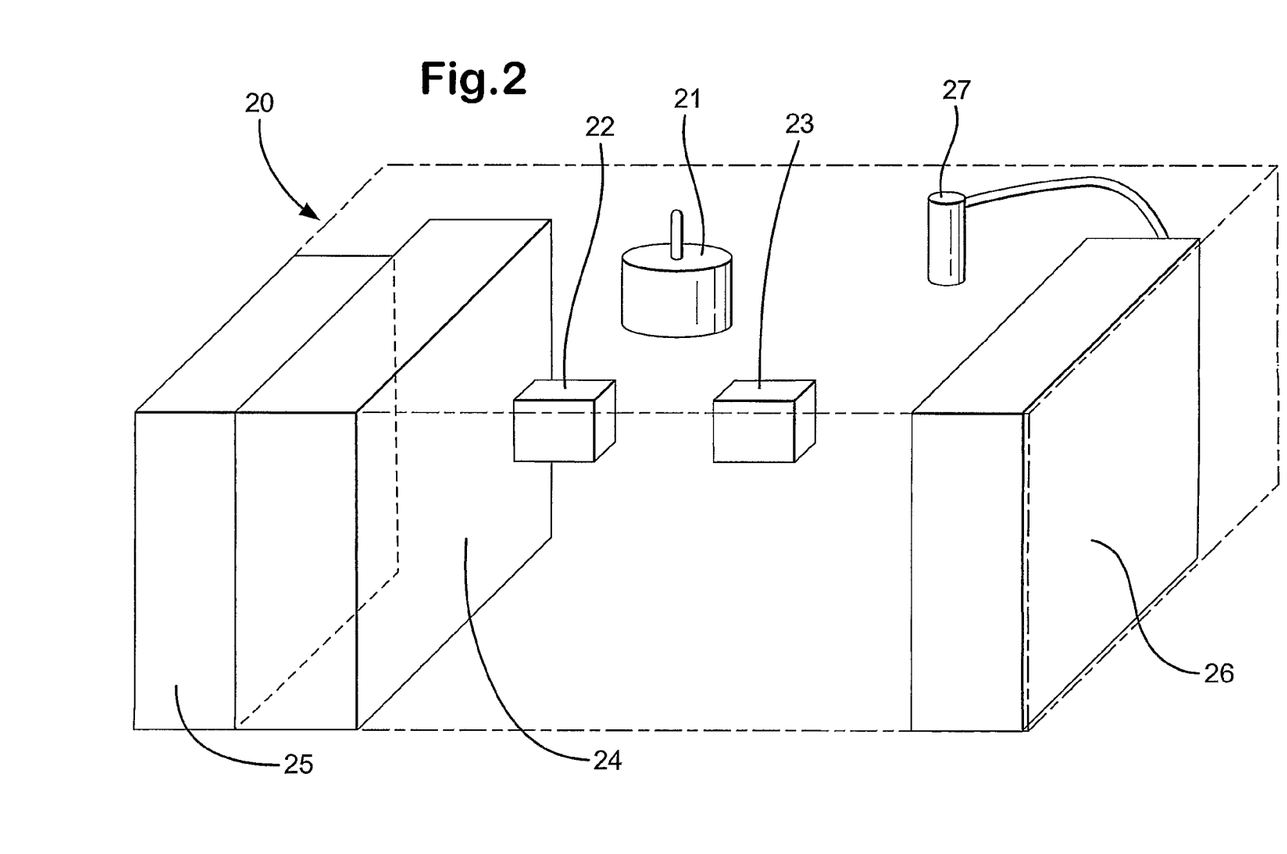
FIG. 2 illustrates an analytical apparatus adapted for use with the sample plate of FIG. 1.

The sample plate of FIG. 1 is adapted to be used with a portable apparatus illustrated schematically in FIG. 2. The portable apparatus shown generally at 20 comprises a micro pump driver 21 adapted to drive the micro pump 4 of FIG. 1; micro valve drives 22 and 23 to operate the valves 5 and 10 of FIG. 1; a micro gas chromatography device and processor unit 24 adapted to communicate with the inlet 9 of FIG. 1; an ASIC (Applications Specific Integrated Circuit) and processor unit 25 adapted to communicate with the acidity sensor 13 of FIG. 1; and a micro NIR spectrometer and processor unit 26 having a probe 27 adapted to communicate with the sample cell 14 of FIG. 1.

Figure 3:
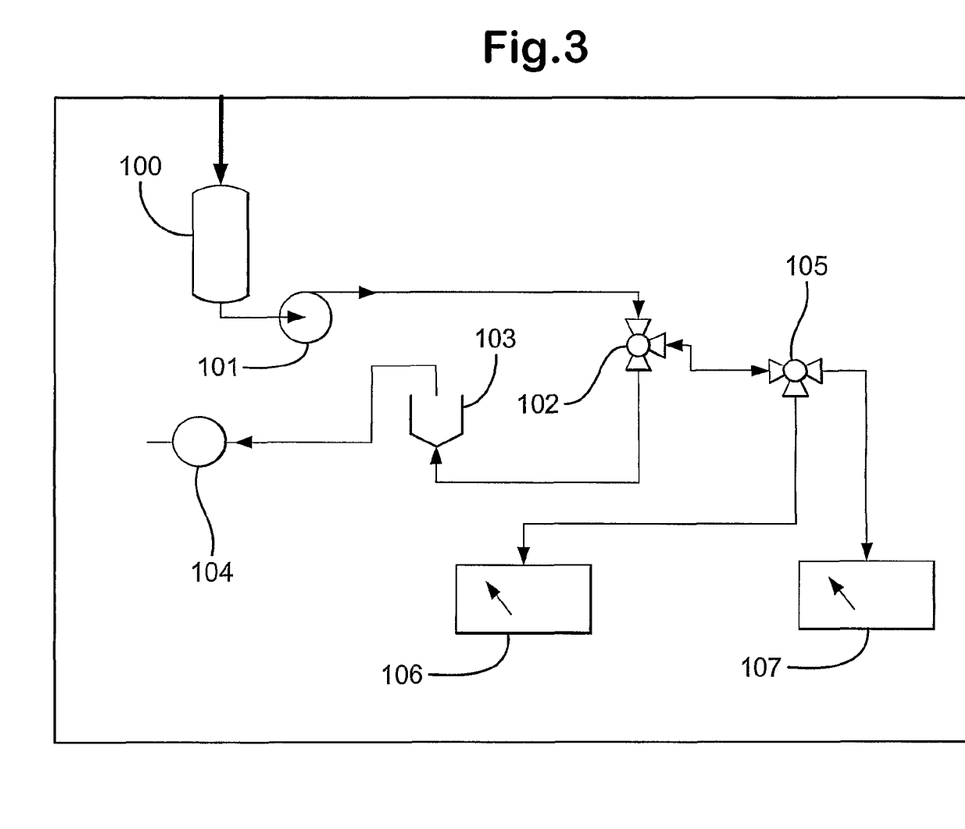
FIG. 3 is a flow sheet showing the various analyses capable of being carried out by an equipment set comprising the sample plate of FIG. 1 together with the analytical apparatus of FIG. 2.

In use, the sample plate 1 of FIG. 1 and the portable apparatus 20 of FIG. 2 are adapted to fit together to produce an equipment set capable of analysing a crude oil sample by gas chromatography, acidity analysis, and NIR, and means (not shown) for connecting the sample plate 1 and the portable apparatus 20 together are provided. A flow-sheet showing the various analysis steps capable of being carried out by the equipment set is shown in FIG. 3. In the process illustrated in FIG. 3, crude oil (100) is metered by a gear pump (101) and routed via a valve (102) to a head space separator (103) to generate vapour which is passed to a micro gas chromatography device (104), or to a second valve 105. The second valve routes the sample to an acidity sensor (106) or a sample cell (107) for a micro NIR device.

Figure 4:
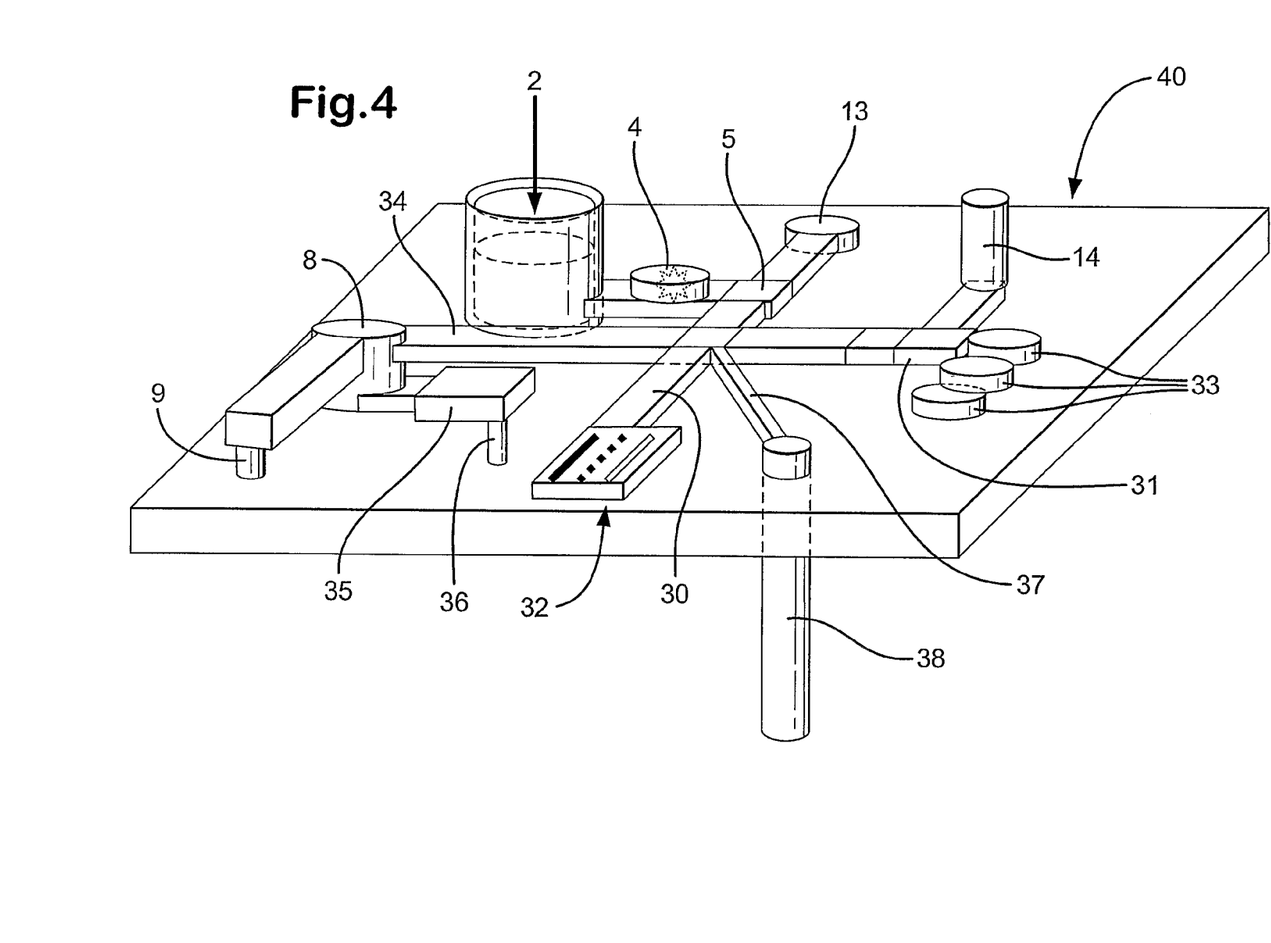
FIG. 4 illustrates a further sample plate according to the invention.

FIG. 4 shows a further embodiment of a sample plate according to the invention. The sample plate, shown generally at 40, contains many of the same elements as shown in FIG. 1, represented by the same numbers. However, output from the micro gear pump 4 is directed to sample preparation devices and on to additional sensors and micro analytical devices. Thus sample is directed to the head space device 8 and the vapour on to the GC inlet 9, and vapour also passes to a microchip 35 having gas chromatography functionality, and thence to an outlet 36. In addition, a fluidic channel 30 transfers crude oil from receiver 2 to a multi function sensor chip 32, capable, for example, of producing a signal indicative of density, viscosity and electrochemical properties. A fluidic channel 31 transfers crude oil from receiver 2 to a plurality of sensors arranged in an array shown generally at 33, capable of detecting various metals and/or specific compounds. A fluidic channel 37 transfers crude oil from receiver 2 to a unit 38 for sample preparation for an aromatics analysis.

Figure 5:
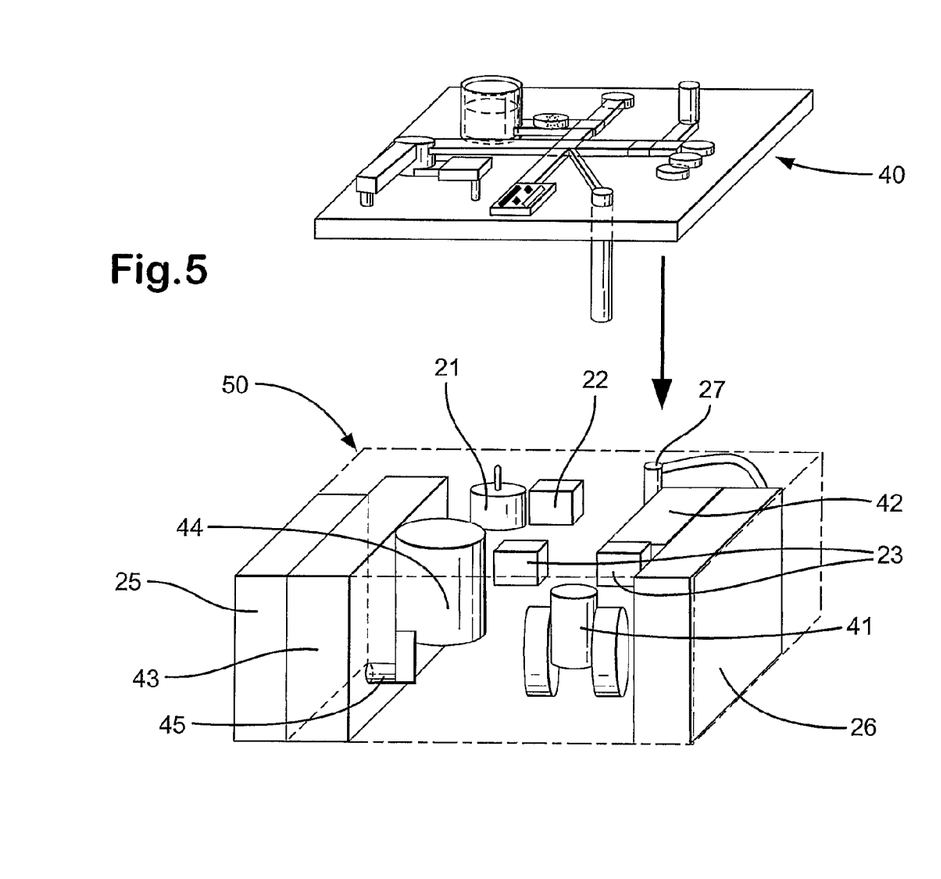
FIG. 5 illustrates an equipment set comprising the sample plate of FIG. 4 in association with an appropriate analytical apparatus.

The sample plate of FIG. 4 is adapted to be used with a portable apparatus, and FIG. 5 shows an exploded view of an equipment set comprising the sample plate 40 of FIG. 4 and a portable apparatus 50. In use, the sample plate 40 and portable apparatus 50 comprise means (not shown) for connecting to each other. The portable apparatus 50 comprises a micro pump driver 21 and micro valve drives 22 and 23; a micro gas chromatography and integrated micro mass spectrometer device 43 adapted to communicate with the outlets 9 and 36 of FIG. 4; a number of ASIC and associated processor units 25 adapted to communicate with sensor 13 and the various sensors on chip 32 of FIG. 4; and a micro NIR spectrometer 26 having a probe 27 adapted to communicate with the sample cell 14 of FIG. 4. In addition, the aromatics unit 38 of FIG. 4 connects with an aromatics analyser 41 and the sensors 33 connect with a reader 42 for specific metals and/or specific compounds. A micro combustor 44 is provided capable of generating, for example, nitrogen oxides and/or sulphur oxides, which are transferred via a connector 45 to a differential ion mobility unit forming part of the GC/MS system 43.

In use, the equipment set of FIG. 5 is capable of analysing a crude oil sample by gas chromatography, acidity analysis, NIR, and differential ion mobility, as well as measuring density, viscosity and electrochemical properties, and analysing for various metals and/or compounds.

The invention claimed is:

1. An equipment set for analysing a fluid selected from a a refinery feedstock, a refinery intermediate and a product of a refinery process, or a component or reaction product thereof, which comprises
   a portable apparatus containing at least two different analytical devices, wherein said at least two different analytical devices include:
   (a) a first analytical device for determination of the boiling point profile of a refinery feedstock, a refinery intermediate or a product of a refinery process, and
   (b) at least one further analytical device associated with a database and an algorithm and capable of measuring at least one physical or chemical property of a refinery feedstock or a product of a refinery process, said equipment set being capable of determining at least the boiling point profile, the total acid number (TAN) and the density of a refinery feedstock or said product of a refinery process;
   wherein said first analytical device and said at least one further analytical device are each selected from a micro-distillation device, a micro-near infrared (NIR) spectrometer, a micro-oscillator device and a micro-gas chromatograph (GC); and
   a sample plate in association with said portable apparatus, which sample plate comprises (i) a receiver for a fluid to be analysed; (ii) at least two fluidic channels each adapted to transfer a portion of said fluid or a component or reaction product thereof from said receiver to one of said analytical devices contained in said portable apparatus; (iii) at least one of: at least one sensor capable of responding to a physical or chemical property of said fluid or a component or reaction product thereof, and at least one sample cell for containing a sample of said fluid or a component or reaction product thereof for spectroscopic or optical analysis; and (iv) at least one additional fluidic channel adapted to transfer a portion of said fluid or a component or reaction product thereof from said receiver to said at least one of: at least one sensor and at least one sample cell.

2. An equipment set according to claim 1, in which the sample plate also comprises means for attachment of said sample plate to said portable apparatus.

3. An equipment set according to claim 1, in which the sample plate also comprises means for linking any sensor and any sample cell in the sample plate to at least one associated electronic circuitry and spectroscopic or optical analysis means which is contained in the portable apparatus.

4. An equipment set according to claim 1, in which the sample plate also comprises a mechanism for permitting sliding or rotating movement of said plate or any part thereof such that in use different parts of said plate may be brought into association with different components of said portable apparatus.

5. An equipment set according to claim 1 in which the sample plate comprises a plurality of sensors or sample cells in the form of an array.

6. An equipment set according to claim 1, in which the sample plate contains at least one fluidic device for at least one of: separation of the fluid to be analysed into components and conversion of the fluid into one or more reaction products.

7. An equipment set according to claim 1, in which the sample plate includes means for storing portions of liquid on the plate.

8. An equipment set according to claim 1, in which the sample plate has one or more micro pumps.

9. An equipment set according to claim 8, in which the one or more micro pumps are selected from gear pumps, diaphragm pumps, syringe pumps and peristaltic pumps.

10. An equipment set according to claim 1, in which the sample plate has one or more microvalves.

11. An equipment set as claimed in claim 1, which includes at least 5 different analytical devices, at least one of which is in the form of a sensor located on the sample plate or which includes a sample cell located on the sample plate.

12. An equipment set as claimed in claim 11, in which any sensor and any sample cell contained in the sample plate is linked with at least one of: associated electronic circuitry and spectroscopic or optical analysis means which is contained in the portable apparatus.

13. An equipment set as claimed in claim 1, which is capable in addition of determining at least one of: total base number, cold flow property, viscosity, Research Octane Number, Motor Octane Number, cetane number, smoke point, Bureau of Mines Correlation Index, refractive index, conductivity, sulphur content, nitrogen content, nickel content, and vanadium content.

14. An equipment set as claimed in claim 1, which comprises at least one of: means for separating a fluid into one or more components prior to analyzing said one or more components and means for converting a fluid into one or more reaction products prior to analysing said one or more reaction products.

15. An equipment set as claimed in claim 1, which also comprises an additional oscillating sensor and an electrochemical sensor.

16. An equipment set as claimed in claim 1, in which one or more portions of the sample plate may in use be at least one of: heated and cooled using at least one of heating and cooling means contained in the portable apparatus.

17. An equipment set as claimed in claim 1, which comprises a plurality of sample plates.

18. An equipment set as claimed in claim 17, in which each of the plurality of sample plates has the same construction.

19. An equipment set as claimed in claim 17, in which the plurality of sample plates includes two or more different types of plates having different construction, the construction of each type of plate being adapted for use with a particular type of fluid or component or reaction product thereof to be analysed.

20. A method of analysing a fluid selected from a hydrocarbon fluid, a refinery feedstock, a refinery intermediate and a product of a refinery process, or a component or reaction product thereof, which comprises carrying out the analysis using an equipment set as claimed in claim 1.

21. A method as claimed in claim 20, in which a refinery feedstock, a refinery intermediate, or the product of a refinery process is analysed.

22. A method as claimed in claim 21, in which the analysis results include at least the boiling point profile, the density, and the total acid number of the fluid or component or reaction product thereof being analysed.

* * * * *